United States Patent [19]

Pedersen et al.

[11] Patent Number: 4,684,469

[45] Date of Patent: Aug. 4, 1987

[54] TWO COMPONENT BIOCIDAL PROCESS

[75] Inventors: Daniel E. Pedersen, Cottage Grove; Herbert J. Hatcher, Eagan, both of Minn.

[73] Assignee: Ecolab Inc., St. Paul, Minn.

[21] Appl. No.: 906,645

[22] Filed: Sep. 11, 1986

Related U.S. Application Data

[63] Continuation of Ser. No. 741,716, Jun. 6, 1985, abandoned, which is a continuation of Ser. No. 495,437, May 17, 1983, abandoned.

[51] Int. Cl.$^4$ ............................ C02F 1/50; C12N 9/28
[52] U.S. Cl. .................................... 210/632; 210/764; 210/928; 424/92; 435/202; 435/204; 162/161
[58] Field of Search ...................... 210/764, 632, 928; 424/92; 435/202, 204, 810; 162/161

[56] References Cited

U.S. PATENT DOCUMENTS

| | | | |
|---|---|---|---|
| 2,673,828 | 3/1954 | Keepsell et al. | 435/198 |
| 2,724,679 | 11/1955 | Tsuchiya et al. | 435/103 |
| 3,033,758 | 5/1962 | Kaufmann et al. | 435/101 |
| 3,391,061 | 7/1968 | McNeely | 435/104 |
| 3,773,623 | 11/1973 | Hatcher et al. | 210/632 |
| 3,824,184 | 7/1974 | Hatcher et al. | 210/600 |
| 4,055,467 | 10/1977 | Christensen et al. | 162/161 |
| 4,317,880 | 3/1982 | Heady | 435/94 |
| 4,370,199 | 1/1983 | Orndorff | 162/161 |

Primary Examiner—Benoit Castel
Attorney, Agent, or Firm—Merchant, Gould, Smith, Edell, Welter & Schmidt

[57] ABSTRACT

A method of use of a two component biocidal preparation suitable for controlling slime, microbial organisms such as bacteria, and fungi in industrial waters is disclosed. The preparation includes a biocide and a polysaccharide degrading enzyme effective against those polysaccharides typically found in industrial waters.

10 Claims, No Drawings

TWO COMPONENT BIOCIDAL PROCESS

This is a continuation of application Ser. No. 741,716 filed June 6, 1985, which is a continuation of application Ser. No. 495,437, filed May 17, 1983, both now abandoned.

FIELD OF THE INVENTION

This invention relates to two component biocidal systems suitable for use in controlling slimes, bacteria, and fungi in industrial waters.

BACKGROUND OF THE INVENTION

The existence of slimes, bacteria and fungi in waters, particularly industrial waters, is an ongoing problem. Examples of industrial waters where slimes and the like can interfere with industrial processes include cooling towers, effluent discharges, waters used for conveying particulate matter, and the like. In particular, pulp and paper mill production waters are affected by resident microflora and the slimes produced by the microflora. These slimes can interfere with the production process, causing nozzle plugging, screen blinding, and sheet defects such as holes and discolorations.

The term slime or slimes refers to a broad range of mucous, viscous, and leathery materials. These materials typically comprise or originate from polymeric, generally polysaccharide excretions produced by a broad spectrum of microorganisms.

Typically, biological deposits of all types including slimes are treated by the addition of biocides or chemicals. Where slimes are present, biocides are frequently added in an effort to destroy the bacteria or microflora population which may produce the slimes. Chemicals which have been used for this purpose include chlorine compounds including the chlorophenates; organomercurial compounds such as phenylmercuric acids; thiocarbamate compounds; thiocyanate compounds such as the isothiocyanates and methylene-bis-thiocyanate; tributyltin oxide; and the like. However, these chemicals tend to be costly and highly toxic in the quantities known to be required for effective control of microbial populations. As a further drawback, most of these chemicals tend to be most effective at an acid pH, such that in more alkaline systems, even greater concentrations are required. Additionally, it appears that no precise correlation exists between the size of the bacterial population and the accumulation of slime. Substantial slime accumulations have been observed even in waters having a low bacterial count. Similarly, high bacterial counts have been observed in waters having no significant slime accumulation. Consequently, use of a biocide may not adequately control biological slime accumulations.

As an alternative to treatment with biocides, it is also known that slime accumulation can be controlled to a certain degree by use of the enzyme levan hydrolase, also known as levanase. It was discovered that levan, a polysaccharide produced by a variety of bacteria, is a significant component of many industrial slimes. U.S. Pat. No. 3,824,184 to Herbert J. Hatcher, discloses the addition of levan hydrolase to industrial waters having a slime accumulation or potential slime problem. The enzyme can hydrolyze the levan present in the slimes, substantially decomposing the slimes and lessening the problems associated with their presence in the water systems. However, the enzyme does nothing to limit or reduce the microbial population.

We have discovered that the combination of a biocide and a polysaccharide degrading enzyme will significantly reduce microbial counts and slime accumulations, far more effectively than a biocide or an enzyme alone.

BRIEF DESCRIPTION OF THE INVENTION

We have discovered a biocidal system including a biocide and a sufficient amount of a polysaccharide degrading enzyme to increase the effectiveness of the biocide.

DETAILED DESCRIPTION OF THE INVENTION BIOCIDE

The biocide component of this invention can include substantially any biocide which will not adversely affect the activity of the enzyme, discussed below. Examples of suitable biocides include chlorophenate compounds such as pentachlorophenates and trichlorophenates; organomercurial compounds such as phenylmercuric acid; carbamate compounds such as methyldithiocarbamates, ethylenebisdithiocarbamates, and dimethyldithiocarbamates; carbonate compounds such as cyanodithioimidocarbonates; thiocyanates such as chloroethylene thiocyanate compounds, and methylene-bis-thiocyanate compounds; and other biocides such as bromo-hydroxyacetophenone compounds; benzothiazole compounds; ethylene diamine compounds, nitrilopropionamides; bromopropionamides; bromo-acetoxybutenes; bromopropanolaldehyde compounds; bis-trichloromethyl sulfones; dimethyl hydantoin compounds; and the like. Mixtures of biocides can also be used.

The biocide methylene-bis-thiocyanate has proven to be particularly effective in the context of this invention, as has a combination of dimethyldithiocarbamate and disodium ethylenebisdithiocarbamate.

The biocides can be obtained from many chemical suppliers such as American Cyanamide, Betz, Beckman, Dearborn Chemical, Economics Laboratory, Inc., Merck, Nalco, Vineland Chemical, and the like.

The concentration of biocide required for effectiveness in this invention varies greatly and can depend upon the conditions such as temperature and pH of the water, the microbial count and the type of industrial water being treated. The lower and upper limits of the required concentrations will substantially depend upon the specific biocide or combination of biocides used. For example, a highly effective biocide can require a concentration of only about 1 or 2 parts biocide to one million parts industrial water (ppm) in the context of this invention, while a quaternary ammonium compound may require a minimum concentration of 75 or 100 ppm. With certain biocides the upper level concentration can reach 600 ppm or more. For three of the previously mentioned biocides, the approximate ranges of concentration for effectiveness in this invention, and a generally preferred range for effectiveness in papermaking processes, is provided below:

| Biocide | Range | Preferred Range |
|---|---|---|
| Methylene-bis-thiocyanate | 5–30 ppm | 15–25 ppm |
| Carbamates | 50–250 ppm | 75–125 ppm |
| Bromopropionamides | 100–400 ppm | 200–300 ppm |

Whether a given concentration will be effective is dependent upon many factors such as the conditions, the particular industrial process, the organic load in the system, machine cleanliness, and the specific biocide or mixture of biocides in use.

Many biocides generally require a much higher concentration to be effective at an alkaline pH than at an acid pH. However, in the context of this invention, even at an alkaline pH, a lower concentration of the biocide in combination with the enzyme will generally be adequate for effective reduction of microbial counts.

ENZYME

The enzyme component of this invention can be any effective polysaccharide degrading enzyme or polysaccharidase. The enzyme chosen should correspond to the problem-causing polysaccharide or polysaccharides present in the water system. For example, the presence of various starch compounds, glycogen compounds, dextran compounds, levan compounds and the like may be undesirable in industrial waters. The enzyme added to a system having any of the these particular polysaccharides present should be one which will hydrolyze that particular polysaccharide. For example, the enzyme could be dextranase, alpha or beta amylase, a levan hydrolase formulation, or the like.

Many microorganisms form an extracellular fructan polysaccharide known as levan. Levan slimes and the microorganisms producing levan are typically present in paper mill production waters and are known to cause serious problems for the pulp and paper industry. An enzyme product containing levan hydrolase or levanase will be effective against slimes or microbial coatings of levan.

By using methods known in the art, the desired enzyme can generally be obtained from the appropriate enzyme-producing microorganisms by providing them with the required nutrient to induce enzyme production. Microorganisms that are known to produce the enzyme levan hydrolase include Rhodotorula sp.; Azotobacter sp., Bacillus sp., Arthobacter sp., Micrococcus sp., and Pseudomonas sp. Levan hydrolase production can typically be induced in these organisms by providing them with the nutrient levan using the appropriate procedures and conditions such as are known. One such method for producing levan hydrolase is disclosed in U.S. Pat. No. 3,773,623. Another method for producing levan hydrolase is disclosed in U.S. Pat. No. 2,673,828.

There are several known methods for producing the required nutrient such as levan, dextran, and the like for use in inducing enzyme production. Methods for producing levan, dextran and the like are disclosed in U.S. Pat. Nos. 3,033,758; 2,673,828; and 3,391,061.

The enzyme component of this invention can comprise a whole cell culture (enzyme crude product), including the enzyme compound itself, the microorganisms which produce the enzyme, and the various fermentation products. Alternatively, the enzyme component can comprise the purified enzyme, obtained, for example, by fractionation. Stabilizing agents such as sodium sulfite or other reducing agents, cellular protein, and propylene glycol or other effective polyalcohols may also be desirable, as is known in the art.

METHOD OF USE

In treating the industrial waters, preferably, the enzyme component is added first to begin degradation of the polysaccharides within the system. The enzyme component can be added using any known method which will provide the desired concentration of enzyme to the waters. An enzyme concentration of at least about 2 parts enzyme at 500 units per ml, per one million parts industrial water, or 4 units of levan hydrolase activity per gallon of industrial water, is typically required for the desired results of this invention.

Typically, the enzyme is intermittently added to the industrial waters. A preferred method is the timed feed, where the appropriate addition is gauged on the water flow characteristics of the system. The enzyme addition rate can be monitored, and maintained at the desired level, by known methods. If the enzyme is added in too large a quantity at one time, the polysaccharide deposits may break free before substantially degrading. Such deposits can interfere with the industrial processes by blocking the system, causing breaks in the paper products, or the like.

The temperature of the industrial waters can affect the activity of the enzyme. Consequently, the preferred water temperature is one where the enzyme will be sufficiently active to produce the desired decrease in slime and microbial populations, at a lowered concentration of biocide. Typically, particularly with levan hydrolase, the desired enzyme activity for rapid hydrolysis occurs at a water temperature between about 75° F. and 150°, or more preferably for reasons of enzyme activity, 90° F. to 135° F.

Typically the enzyme is sold as an enzyme crude product, in liquid form, in packaging such as 55-gallon drums. It is also envisioned that the enzyme crude product could be sold in a dried form, for example, by units of enzyme activity per pound, where the enzyme or enzyme crude product has been dried onto an insoluble substrate such as a protein.

In process waters, the stock of biocide is preferably slug fed, although any other appropriate method of adding it to the system may be used. However, a continuous feed of biocide may result in the overgrowth of microorganisms which are resistant to the biocidal agent.

The biocide component is typically sold in drums, cartons, or other packaging, in liquid or dry form in varying concentrations, as is known in the art.

It is often preferable that the enzyme and the biocide be fed to separate parts or machines in the system because some biocides can be harmful at high concentrations to the enzyme.

The following specific Examples which include the best mode were prepared and tested as described.

EXAMPLE I

Into each of six duplicate 250 ml shake flasks was charged 50 ml Difco nutrient broth medium. The medium was inoculated from a slant of *Aerobacter levanicum*. The flasks were shaken for one hour at 30° C. to accelerate growth of the microorganisms. The flasks were then set aside for an incubation period of about 48 hours at 30° C. After the incubation period, the flasks were shaken briefly and samples were taken for an initial zero time plate count. As indicated in Table 1, to four of the six flasks was added a stated amount of a whole cell culture containing the enzyme levan hydrolase at a concentration of 500 units per ml. A unit of levan hydrolase activity is that amount of liquid or powder that will form 0.35 micrograms of fructose per minute from the levan substrate. All flasks were then shaken for ½ hour at 30° C. on a rotary shaker operating at approximately 150 rpm. As further indicated in Table 1, four of the six flasks then received an addition of the stated amount of methylene-bis-thiocyanate. The flasks were again placed on the shaker for about 4 hours and plate counts were made.

The results were as follows:

TABLE 1

| Methylene bis-thio-cyanate (ppm) | Whole Cell Culture Containing Levan Hydrolase (ppm) | Colony Forming Units |
|---|---|---|
| 35 | 0 | $3.6 \times 10^4$ |
| 35 | 21 | $2.8 \times 10^2$ |
| 40 | 0 | $2.5 \times 10^4$ |
| 40 | 21 | $1.8 \times 10^1$ |
| 0 | 21 | $2.2 \times 10^9$ |
| 0 | 0 | $9.7 \times 10^8$ |

Surprisingly, the combination of the biocide plus levan hydrolase resulted in substantially fewer colony forming units than the expected additive result of the biocide alone plus levan hydrolase in the whole cell culture.

EXAMPLES II–VII

For each Example four duplicate 250 ml shake flasks containing 50 ml Difco nutrient broth medium and 0.5% (by weight) sucrose were inoculated from slant cultures of *Aerobacter levanicum, Rhodotorula glutinis,* or *Bacillus subtilis.* The flasks were shaken on a rotary shaker at approximately 150 rpm for 30 minutes at 30° C. They were then removed to a 30° C. incubator, for incubation as stationary cultures for approximately 24 hours (in the use of *Bacillus subtilis*, the cultures were incubated with slow agitation (30 rpm) rather than as a stationary culture, and for about 18 hours rather than 24 hours). At the end of the stationary incubation period, samples were taken for zero time plate counts. As indicated in the Tables, to two of the flasks was added the stated amount of a whole cell culture containing levan hydrolase at a concentration of approximately 500 units/ml. These flasks were shaken on the rotary shaker at 150 rpm and 30° C. for ½ hour. As further indicated in the Tables, to two of the flasks, including one which had been treated with the whole cell culture, was added the stated biocide at the stated concentration. All four flasks were then placed on the rotary shaker for mixing for 5 minutes. They were then incubated as stationary cultures at 30° C. for approximately 2½ hours. Standard plate counts were then taken on the contents of all four flasks. The plate counts were read after 48–72 hours of incubation at 30° C. The results were as follows:

EXAMPLE II

Methylene-bis-thiocyanate (MBT) and Whole Cell Culture Containing Levan Hydrolase (LH): Effects on Viability of *Aerobacter levanicum*

| MBT | LH | Colony Forming Units |
|---|---|---|
| 20 ppm | 0 | $1.4 \times 10^9$ |
| 20 ppm | 40 ppm | $1.2 \times 10^6$ |
| 0 ppm | 40 ppm | $6.9 \times 10^9$ |
| 0 ppm | 0 ppm | $4.3 \times 10^9$ |

EXAMPLE III

Methylene-bis-thiocyanate (MBT) and Whole Cell Culture Containing Levan Hydrolase (LH): Effects on Viability of *Rhodotorula glutinis*

| MBT | LH | Colony Forming Units |
|---|---|---|
| 10 ppm | 0 ppm | $4.7 \times 10^4$ |
| 10 ppm | 40 ppm | $9.0 \times 10^1$ |
| 0 ppm | 40 ppm | $4.6 \times 10^8$ |
| 0 ppm | 0 ppm | $3.0 \times 10^8$ |

EXAMPLE IV

Methylene-bis-thiocyanate and Whole Cell Culture Containing Levan Hydrolase (LH): Effects on Viability of *Bacillus subtilis*

| MBT | LH | Colony Forming Units |
|---|---|---|
| 20 ppm | 0 ppm | $1.6 \times 10^4$ |
| 20 ppm | 40 ppm | $2.0 \times 10^3$ |
| 0 ppm | 40 ppm | $5.6 \times 10^7$ |
| 0 ppm | 0 ppm | $1.2 \times 10^7$ |

EXAMPLE V

Dimethyl Dithiocarbamate (13%), Disodium Ethylbisdithiocarbamate (15%) (Carbamate) and Whole Cell Culture Containing Levan Hydrolase (LH): Effects on Viability of *Aerobacter levanicum*

| Carbamate | LH | Colony Forming Units |
|---|---|---|
| 200 ppm | 0 ppm | $6.0 \times 10^5$ |
| 200 ppm | 40 ppm | $4.0 \times 10^2$ |
| 0 ppm | 40 ppm | $8.4 \times 10^9$ |
| 0 ppm | 0 ppm | $6.3 \times 10^9$ |

EXAMPLE VI

Dimethyl Dithiocarbamate (13%), Disodium Ethylbisdithiocarbamate (15%) and While Cell Culture Containing Levan Hydrolase (LH): Effects on Viability of *Rhodotorula gultinis*

| Carbamate | LH | Colony Forming Units |
|---|---|---|
| 100 ppm | 0 ppm | $4.1 \times 10^6$ |
| 100 ppm | 40 ppm | $6.0 \times 10^5$ |
| 0 ppm | 40 ppm | $8.4 \times 10^7$ |
| 0 ppm | 0 ppm | $2.1 \times 10^7$ |

EXAMPLE VII

Dimethyl Dithiocarbamate (13%), Disodium Ethylenebisdithiocarbamate (15%) and Whole Cell Culture Containing Levan Hydrolase (LH): Effects on Viability of *Bacillus substilis*

| Carbamate | LH | Colony Forming Units |
|---|---|---|
| 100 ppm | 0 ppm | $1.0 \times 10^3$ |
| 100 ppm | 40 ppm | $5.0 \times 10^1$ |
| 0 ppm | 40 ppm | $8.9 \times 10^7$ |
| 0 ppm | 0 ppm | $1.2 \times 10^7$ |

Examples II through VII show significantly fewer colony forming units present in the growth medium treated with the combination of biocide and the whole cell culture containing levan hydrolase, compared to the use of the biocide alone, the levan hydrolase alone, or no treatment whatsoever.

EXAMPLES VIII AND IX

For each Example, four duplicate 250 ml shake flasks containing 50 ml Difco nutrient broth medium and 0.5% by weight sucrose were inoculated from a slant culture of Sphaerotilus. To the flask was then added and hand shaken, 5% by weight of a levan solution containing 5 g. levan per 100 g. total solution. The cells were allowed to incubate for 24 hours at room temperature. After the incubation period, the stated amount of a whole cell culture containing levan hydrolase (500 units per ml) was added and the mixture was briefly hand shaken. After 2 hours, the stated amount of biocide was added to the flasks and they were briefly hand shaken. The mixture was allowed to rest at room temperature. After 2 hours, plate counts of surviving cells were made, with the results as shown in the Tables.

EXAMPLE VIII

Methylene bis thiocyanate (MBT) and Whole Cell Culture Containing Levan Hydrolase (LH): Effects on Viability of Sphaerotilus

| MBT | LH | Colony Forming Units |
|---|---|---|
| 10 ppm | 0 ppm | $5.3 \times 10^4$ |
| 10 ppm | 40 ppm | $4.7 \times 10^3$ |
| 0 ppm | 40 ppm | $9.8 \times 10^7$ |
| 0 ppm | 0 ppm | $8.6 \times 10^6$ |

EXAMPLE IX

Sodium dimethyl dithiocarbamate (DTC) and Whole Cell Culture Containing Levan Hydrolase (LH): Effects on Viability of Sphaerotilus

| DTC | LH | Colony Forming Units |
|---|---|---|
| 100 ppm | 0 ppm | $4.5 \times 10^4$ |
| 100 ppm | 40 ppm | $6.8 \times 10^3$ |
| 0 ppm | 40 ppm | $5.3 \times 10^7$ |
| 0 ppm | 0 ppm | $2.0 \times 10^7$ |

The test results show that the combination of biocide and a whole cell culture containing levan hydrolase is significantly more effective against Sphaerotilus than is biocide alone, levan hydrolase alone, or no treatment whatsoever.

While we do not wish to be limited to any theory, we have learned that most bacteria which secrete polysaccharides such as levan, develop a capsular polysaccharide layer covering the cell surface. The polysaccharide layer can protect the bacteria from the action of biocides. Other microorganisms present in a medium containing polysaccharide producing bacteria also tend to become coated with a similar protective layer, possibly due to the solubility of most such polysaccharides. Thus, other microorganisms in addition to the polysaccharide producing bacteria develop resistance to biocidal compositions.

We have also discovered that the appropriate enzyme can degrade or destroy the protective layer and significantly enhance the efficacy of a biocide, such that significantly less biocide is required to reduce microbial counts to a satisfactory level. At the same time the enzyme will act upon the slimes, hydrolyzing the polysaccharide component.

The above discussion and Examples provide the detailed discussion of the invention. However, since may embodiments of the invention can be made without departing from the spirit and scope of the invention, the invention resides wholly in the claims hereinafter appended.

We claim:

1. A method to substantially increase the antimicrobial activity of a biocide comprising combining in an industrial water stream a biocide selected from the group consisting of a quaternary ammonium compound, a bromopropionamide, a nitrilopropionamide, a chlorophenate, a benzothiazol, a thiocyanate, a thiocarbamate, and mixtures thereof; and an amount of a polysaccharide-degrading enzyme effective to cooperate with the biocide to substantially increase the antimicrobial activity of the biocide against polysaccharide-producing bacteria, wherein the biocide is intermittently added to the industrial water to maintain a concentration of about 1 to 600 ppm, and wherein the concentration of the enzyme is monitored, and maintained at a level of at least about 2 ppm, said enzyme being derived from a preparation having an enzyme activity of at least about 500 units per milliter.

2. The process of claim 1 wherein the biocide is methylene-bis-thiocyanate.

3. The process of claim 1 wherein the biocide is dimethyl dithiocarbamate.

4. The process of claim 1 wherein the biocide is disodium ethylene-bis-dithiocarbamate.

5. The process of claim 1 wherein the enzyme is an amylase.

6. The process of claim 1 wherein the enzyme is a dextran degrading enzyme.

7. The process of claim 1 wherein the enzyme is a levan hydrolase.

8. The process of claim 7 wherein the temperature of the industrial water is from about 75° to about 150° F.

9. The process of claim 1 wherein the industrial water comprises a white water of a paper making process, and the biocide is added to the white water in an amount which will not adversely affect the paper making process.

10. The process of claim 1 wherein the enzyme is added to the industrial water prior to the addition of any significant amount of the biocide.

* * * * *

UNITED STATES PATENT AND TRADEMARK OFFICE
CERTIFICATE OF CORRECTION

PATENT NO. : 4,684,469

DATED : August 4, 1987

INVENTOR(S) : Daniel E. Pedersen et al.

It is certified that error appears in the above-identified patent and that said Letters Patent is hereby corrected as shown below:

Col. 2, lines 15-16 for
"Detailed Description of the Invention Biocide" read
--Detailed Description of the Invention
             Biocide--

Col. 2, line 38, for "ethylenebisdithiocarbamate" read
--ethylbisdithiocarbamate--.

Col. 3, line 41, for "Arthobactersp.," read
--Arthobacter sp.,--.

Col. 6, line 45, for "gultinis" read --glutinis--.

Col. 6, line 59, for "substilis" read --subtilis--.

Signed and Sealed this

Sixteenth Day of February, 1988

Attest:

DONALD J. QUIGG

Attesting Officer

Commissioner of Patents and Trademarks